US006627393B2

(12) United States Patent
Segall et al.

(10) Patent No.: US 6,627,393 B2
(45) Date of Patent: *Sep. 30, 2003

(54) SOLUTIONS FOR USE AS PLASMA EXPANDERS AND SUBSTITUTES

(75) Inventors: Paul E. Segall, Berkeley, CA (US); Hal Sternberg, Berkeley, CA (US); Harold D. Waitz, Berkeley, CA (US); Judith M. Segall, Berkeley, CA (US)

(73) Assignee: BioTime, Inc., Berkeley, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/475,463

(22) Filed: Dec. 30, 1999

(65) Prior Publication Data

US 2003/0022147 A1 Jan. 30, 2003

Related U.S. Application Data

(63) Continuation-in-part of application No. 08/896,824, filed on Jul. 18, 1997, now Pat. No. 6,444,418, which is a continuation of application No. 08/253,384, filed on Jun. 3, 1994, now Pat. No. 5,702,880, which is a continuation-in-part of application No. 08/133,527, filed on Oct. 7, 1993, now abandoned, which is a continuation-in-part of application No. 08/071,533, filed on Jun. 4, 1993, now Pat. No. 5,407,428.

(51) Int. Cl.$^7$ .............................. A01N 1/00; A01N 1/02
(52) U.S. Cl. .............................. 435/1.2; 435/1.1; 435/2
(58) Field of Search ........................... 435/1.1, 1.2, 1.3, 435/2

(56) References Cited

U.S. PATENT DOCUMENTS

| | | | |
|---|---|---|---|
| 3,937,821 A | 2/1976 | Irikura et al. ................. 424/180 |
| 3,949,098 A | 4/1976 | Bangert ....................... 426/324 |
| 4,001,401 A | 1/1977 | Bonsen et al. ................ 424/177 |
| 4,061,736 A | 12/1977 | Morris et al. ................. 424/177 |
| 4,216,205 A | 8/1980 | Radowitz ..................... 424/101 |
| 4,663,166 A | 5/1987 | Veech .......................... 424/146 |
| 4,908,350 A | 3/1990 | Kramer et al. .................. 514/2 |
| 4,923,442 A | 5/1990 | Segall et al. ................... 604/52 |
| 4,927,806 A | 5/1990 | Kramer et al. .................. 514/2 |
| 5,082,831 A | 1/1992 | Leaf et al. .................... 514/56 |
| 5,084,377 A | 1/1992 | Rowan et al. .................. 435/1 |
| 5,120,719 A | 6/1992 | Iwamoto et al. ............... 514/54 |
| 5,130,230 A | 7/1992 | Segall et al. ................... 435/1 |
| RE34,077 E | 9/1992 | Segall et al. ................... 604/52 |
| 5,171,526 A | 12/1992 | Wong et al. ................... 422/28 |
| 5,374,624 A | 12/1994 | Segel .......................... 514/21 |
| 5,407,428 A | 4/1995 | Segall et al. ................... 604/28 |
| 5,571,801 A | * 11/1996 | Segall et al. ................... 514/59 |
| 5,702,880 A | * 12/1997 | Segall et al. .................. 435/1.2 |
| 5,945,272 A | * 8/1999 | Segall et al. .................. 435/1.2 |

FOREIGN PATENT DOCUMENTS

JP            48-30376      * 9/1973

OTHER PUBLICATIONS

Smirnova et al. Probl. Gematol. Pereliv. Krovi. 1971. vol. 16 (10), pp. 36–42, CAPLUS Abstract enclosed.*
Ura et al. J. Wakyama Medical Society. 1974. vol. 25, No. 3, pp. 307–320, EMBASE Abstract enclosed.*
Kumiko et al. Circulation Control. 1989. vol. 10, No. 2, pp. 255–262, JICST–EPLUS Abstract enclosed.*
Ryu et al. Circulation Control. 1990. vol. 11, No. 1, pp. 107–111. JICST–EPLUS Abstract enclosed.*
Belzer, F.O. et al., (1985) "Combination Perfusion–Cold Storage for Optimum Cadaver Kidney Function and Utilization," *Transplantation* 39 : 118–121.
Bishop, M.C. and Ross, B.D., (1978) "Evaluation of Hypertonic Citrate Flushing Solution for Kidney Preservation Using the Isolated Perfused Rat Kidney," *Transplantation* 25 : 235–239.
Collins, G.M., (1969) Hypothermic Kidney Storage, *Transplantation Proceedings* IX : 1529–1534.
Kallerhoff, M. et al., (19850 " Effects of Preservation Conditions and Temperature on Tissue Acidification in Canine Kidneys," *Transplantation* 39 : 485–489.
Messmer, K. "Characteristics, Effects and Side–Effects of Plasma Substitutes," *Bodensee Symposium on Microcirculation* (Hammersen and Messmer, eds.), Karger, N.Y., p. 51–70 (1989).
Ross, H. et al., (1976) "72–Hr Canine Kidney Preservation Without Continuous Perfusion," *Transplantation* 21 : 498–510.
Spahn, D.R. et al., (1994) "Cardiovascular and Coronary Physiology of Acute Isovolemic hemodilution: A revies of Nonoxygen–Carrying and Oxygen–Carrying Solutions," *Anesth. Analg.* 78: 1000–1021.

(List continued on next page.)

Primary Examiner—Christopher R. Tate
(74) Attorney, Agent, or Firm—Bret E. Field; Bozicevic, Field & Francis

(57) ABSTRACT

An artificial plasma-like substance having at least one water soluble polysaccharide oncotic agent selected from the group consisting of high molecular weight hydroxyethyl starch, low molecular weight hydroxyethyl starch, dextran 40 and dextran 70, which is buffered by lactate and has a pre-administration pH of between 4 and 6.5 is disclosed. In one embodiment, the artificial plasma-like solution may have at least two water soluble polysaccharide oncotic agents one of which is eliminated from the circulation slowly and the other of which is eliminated from the circulation quickly. Supplementation of the plasma-like solution with certain ions is described. A system for administration of the plasma-like solution to a subject wherein the system comprises a first and second solution each having particular buffers is described. Methods for the administration of the plasma-like solution are also disclosed.

34 Claims, No Drawings

OTHER PUBLICATIONS

Wall, W.J., (1977) "Simple Hypothermic Preservation for Transporting Human Livers Long Distances for Transplantation," *Transplantation* 23: 210–216.

*ATCC Catalogue of Bacteria and Bacteriophages*, (1992) p. 486, Medium 1590.

Lehninger, A. (1982) "Digestion, Transport, and the Integration of Metabolism," *Principles of Biochemistry* Chapter 24, Part III, pp. 705–713.

Wagner et al., (1993) "Pharmacolgic and Clinical Considerations in Selecting Crystalloid, Colloidal, and OxygenCarrying Resuscitation Fluids," *Clinical Pharmacy* 12: 335–346.

Fisher, J.H. et al., (1985) Flush Solution 2, A New Concept for One–to–Three–Day Hypothermic Renal Storage Preservation, *Transplantation* 39: 122–126.

Sprung, J. et al., (1991) "Effects of Acute Hypothermia and Adrenergic receptor Blockade on Serum Potassium Concentration in Rats," *Critical Care Medicine* 19: 1545–1551.

Bailes et al., (1990) "The Use of Ultra–profound Hypothermia in a Totally Exsanguinated and Blood–Substituted Canine Mode. I," *Cyrobiology* 27: 622–623.

Elrifai et al., (1990) "The Use of Ultra–profound Hypothermia in a Totally Exsanguinated and Blood–Substituted Canine Model. II," *Cyrobiology* 27: 622–623.

Boerema et al., "Life Without Blood," *J. Cardiovasc. Surg.* 13: 133–146.

Fischbach, F., "Chemistry Studies: Potassium (K)," *A. Manual of Laboratory Diagnostic Tests*, Third Edition, Chapter 6, pp. 254–257. (1988).

Smith, A., (1956) "Studies on Golden Hamsters During Cooling to and Rewarming from Body Temperatures Below 0° C.," *Proceedings of the Royal Society* 145: 391–442.

Leavitt, et al. (1990) "Surivival from Prolonged cardiac Arrest in Totally Exsanguinated Hypothermic Dogs," *Abstracts: Federation ofAmerican Societies for Experimental Biology* Part 2, 4048.

Segall et al., (1987) "Ice–Cold Bloodless Dogs Revived Using Protocol Developed in Hamsters," *Abstracts: Federation of American Societies for Experimental Biology* 5959.

Segall et al., (1991) "Animal Models in Ice–Cold Bloodless Medicine," *Abstracts: The FASEB Journal* Part I, 147.

Sternberg, et al., (1990) "Interventive Gerontology, Cloning and Cryonics," *Biomedical Advances in Aging Chpt.* 19:207–219.

Sternberg, et al., (1991) "Partly–Frozen Overnight, Thawed Hamsters' Hearts Beat," 1991 FASEB Abstract Form.

Storey, K.B. and Storey, J.M., (1990) "Frozen and Alive," *Scientific American* 263(6): 92–97.

Waitz et al., (1991) "Hamsters Live After Hours of Bloodless Hyperbaric $O_2$," *Abstracts: The FASEB Journal Part II*, 4375.

Bishop et al., (1978) "Evaluation of Hypertonic Citrate Flushing Solution for Kidney Preservation Using the Isolated Perfused Rat Kidney," *Transplantation* 25:235.

"10% LMD in 5% Dextrose Injection . . . ," Product Information Sheet, Abbott Laboratories, North Chicago, IL.

"6% Dextran 70 in 5% Dextrose Injection . . . ," Product Information Sheet, (1987) Abbott Laboratories, North Chicago, IL.

* cited by examiner

SOLUTIONS FOR USE AS PLASMA EXPANDERS AND SUBSTITUTES

CROSS-REFERENCE TO RELATED APPLICATIONS

This application is a continuation-in-part of application Ser. No. 08/896,824 filed Jul. 18, 1997 and now issued U.S. Pat. No. 6,444,418; which application is a continuation of application Ser. No. 08/253,384 filed Jun. 3, 1994 and now issued as U.S. Pat. No. 5,702,880; which application is a continuation-in-part of application Ser. No. 08/133,527 filed Oct. 7, 1993 and now abandoned; which application is a continuation-in-part of application Ser. No. 08/071,533 filed Jun. 4, 1993 and now issued as U.S. Pat. No. 5,407,428; the disclosures of which applications are herein incorporated by reference.

INTRODUCTION

1. Field of the Invention

The invention relates to the field of plasma-like solutions which may be used to treat hypovolemic subjects or to substitute for the blood or plasma of a subject.

2. Background

Perfusion solutions and blood substitutes are known. The blood substitutes of Collins et al, Kidney preservation for transplantation. Lancet 1219–1222 (1969); Collins G. M., Hypothermic kidney storage. Transplant. Proc. I:1529 (1977); Filcher et al, Flush solution 2, a new concept for one to three day hypothermic renal storage preservation. Transplantation 39:2, 122–126 (1985); Robs et al, 72-hour canine kidney preservation without continuous perfusion. Transplantation 21:498 (1976); Sacks et al, Transplantation 19:283 (1974) and Kallerhoff et al, Effects of the preservation conditions and temperature on tissue acidification in canine kidneys. Transplantation 39:5, 485–489 (1985) all consist only of low molecular weight molecules that readily traverse the capillary bed of the subject and thus are generally incapable of maintaining proper ionic or fluid balance or plasma volume when used in an intact mammalian subject.

Klebanoff and Phillips, Cryobiology 6:121–125 (1969) disclosed hypothermic asanguinous perfusion of dogs with 11 of 15 subjects surviving up to 95 minutes when perfused with buffered Ringer's lactate at 7.1 to 16 degrees C. (44.6–60.4 degrees F.).

Those blood substitutes that have an impermeable substance to maintain volume use human serum albumin or a mixture of plasma proteins, as the impermeate molecule to maintain blood volume. These are disclosed in Wall et al., Simple hypothermic preservation for transporting human livers long distances for transplantation, Transplantation, 23:210 (1977); Belzer et al., Combination perfusion-cold storage for optimum cadaver kidney function and utilization, Transplantation 39:2, 118–121, (1985). Haff et al., Journal of Surgical Research 19:1, 13–19 (1975) describe the asanguineous hypothermic perfusion of dogs using two solutions: the first, a flush solution comprised of pooled delipidated homologous plasma and electrolytes, and the second comprised of pooled delipidated homologous plasma, electrolytes and additional potassium chloride at a concentration of 10 milliEquivalents/liter (mEq/l). Haff et al also disclose the use of a pulsatile pump oxygenator and hypothermic perfusion with their solutions and suggest that the procedures could be used for long distance transport of cadaver organ donors and as an alternative to hypothermic circulatory arrest for blood-free intricate surgery.

Non plasma-based solutions for organ preservation are disclosed in Bishop et al., Evaluation of hypertonic citrate flushing solution for kidney preservation using the isolated perfused rat kidney. Transplantation 25:5, 235–239 (1978). This article discloses a perfusion solution that included 50 g/liter dextran 40, a concentration that differs markedly from those of the solutions of the present invention. In addition, the electrolyte and ion concentrations differ markedly from those disclosed for the present invention.

Segall et al., Federation Proceedings 44(3):623, (1985) disclose that a Ringer's lactate-based heparinized blood substitute containing 6% dextran 40 was used to lower the body temperature of hamsters prior to the circulation of cold-protective solutions, which are not disclosed, for 1 to 1.5 hours.

Segall et al., (1987) Federation Proceedings, page 1338, disclose that a blood substitute, which included dextrose (180 mg/dl) and 25 mM HEPES, was used to perfuse a dog to 3° C. when perfusion was stopped entirely. There is no disclosure of the complete composition of the blood substitute.

Segall et al, U.S. Pat. No. 4,923,442 and the reissue thereof disclose a number of solutions used in blood substitution of living subjects all of which include at least some concentration of a cardioplegia agent, usually potassium ion. Segall et al., U.S. Pat. No. 4,923,442 also discloses surgical methods, particularly in respect to instrument placement and the control of pulmonary wedge pressure generally applicable to perfusion of subjects. U.S. Pat. No. 4,923,442 and its reissue are incorporated herein by reference.

Segall et al., U.S. Pat. No. 5,130,230 discloses a blood substitute which may be used as a system of solutions in which a number of solutions, in some embodiments two solutions and in other embodiments four solutions, are used sequentially to completely replace the blood of living subjects. In one of the embodiments, one of the solutions, identified as the recovery solution, of a four solution system is disclosed as having, in addition to several dissolved salts and other constituents, dissolved potassium chloride in a concentration range of 0 to 10 mM. In describing the blood substitute, the specification of U.S. Pat. No. 5,130,230 discloses that the blood substitute comprises "an aqueous solution of electrolytes at physiological concentration, a macromolecular oncotic agent, a biological buffer having a buffering capacity in the range of physiological pH, simple nutritive sugar or sugars, magnesium ion in a concentration sufficient to substitute for the flux of calcium across cell membranes. The blood substitute also includes the forgoing solution and a cardioplegia agent such as potassium ion in a concentration sufficient to prevent or arrest cardiac fibrillation." Thus potassium ion at physiological concentration is part of the base solution of the disclosed blood substitute. The specification also discloses that concentration of cations including $Mg^{++}$, $Ca^{++}$ and $K^+$ in excess of that normally found in mammalian blood are suitable for exerting a cardioplegia effect. Lastly the specification discloses that the blood substitute may be used as a blood volume expander and that "(f)urthermore if the blood substitute according to the invention is used as a blood volume expander in a subject at non-hypothermic temperatures, the cardioplegia agent described . . . will generally be omitted so that normal cardiac function can be maintained." From the forgoing it is clear that the blood substitute when used as a blood volume expander at normal body temperatures contains $K^+$ at physiological concentrations but not in concentrations sufficient to cause cardioplegia.

Commercial products used for the treatment of hypovolemic patients are known and include Hespan (6% hetastarch 0.9% Sodium chloride Injection [Dupont Pharmaceuticals, Wilmington Del.]), Pentaspan (10% pentastarch in 0.9% Sodium chloride Injection [Dupont Pharmaceuticals, Wilmington Del.]) and Macrodex (6% Dextran 70 in 5% Dextrose Injection or 6% Dextran 70 in 0.9% Sodium chloride Injection [Pharmacia, Inc. Piscataway, N.J.]) and Rheomacrodex (10% Dextran 40 in 5% Dextrose Injection or 10% Dextran 40 in 0.9% Sodium chloride Injection [Pharmacia, Inc. Piscataway, N.J.]). These products are known to the medical community for particular FDA approved indications and are extensively described in the volume entitled Physicians' Desk Reference, published annually by Medical Economics Company Inc.

Water-soluble and aqueous colloid preparations of vitamin K are known and are sold respectively under generic names menadiol sodium diphosphate (tradename SYNKAVITE®) and phytonadione MSD, USP (tradename AquaMEPHYTON®) by Roche Labs and Merck Sharp & Dohme, respectively.

SUMMARY AND OBJECTS OF THE INVENTION

It is an object of the invention to provide a blood plasma expander comprising a water soluble polysaccharide oncotic agent supplemented with calcium chloride at physiological concentration.

It is a further object of the invention to provide a blood plasma expander comprising a water soluble polysaccharide oncotic agent supplemented with sodium chloride at physiological concentration and magnesium ion at sub-physiological concentration.

It is a yet further object of the invention to provide a blood plasma expander comprising a water soluble polysaccharide oncotic agent supplemented with sodium chloride at physiological concentration and magnesium ion at sub-physiological concentration and potassium ion at sub-physiological concentration.

Another object of the invention to provide a blood plasma expander comprising at least two water soluble polysaccharide oncotic agents one of which is eliminated from the circulation slowly and the other of which is eliminated from the circulation quickly.

Yet another object of the invention is to provide a buffered blood plasma substitute comprising a water soluble polysaccharide oncotic agent.

A yet further object of the invention is to provide a blood plasma substitute comprising a water soluble polysaccharide oncotic agent buffered by lactate and supplemented with sodium chloride at physiological concentration.

Still another object of the invention is to provide a blood plasma substitute comprising a water soluble polysaccharide oncotic agent buffered by lactate and sodium bicarbonate and supplemented with sodium chloride at physiological concentration.

Still yet another object of the invention is to provide a blood plasma substitute comprising at least two water soluble polysaccharide oncotic agents one of which is eliminated from the circulation slowly and the other of which is eliminated from the circulation quickly, wherein the blood plasma substitute is buffered and supplemented with sodium chloride at physiological concentration.

It is yet another object of the invention to provide a method for expanding the blood volume of a subject in need thereof by administering intravenously to such subject a blood plasma expander comprising a water soluble polysaccharide oncotic agent supplemented with sodium chloride and calcium chloride at physiological concentration.

Still a further object of the invention is to provide a method for expanding the blood volume of a subject in need thereof by administering intravenously to such subject a blood plasma expander comprising at least two water soluble polysaccharide oncotic agents one of which is eliminated from the circulation slowly and the other of which is eliminated from the circulation quickly.

Yet another object of the invention is to provide a method of substituting the blood plasma of a subject in need thereof by administering intravenously to such subject a blood plasma substitute comprising a water soluble polysaccharide oncotic agent buffered by lactate and supplemented with sodium chloride at physiological concentration.

Still yet another object of the invention is to provide a method of substituting the blood plasma of a subject in need thereof by administering intravenously to such subject a blood plasma substitute comprising a water soluble polysaccharide oncotic agent buffered by lactate and sodium bicarbonate and supplemented with sodium chloride at physiological concentration.

Yet still another object of the invention is to provide a method of substituting the blood plasma of a subject in need thereof by administering intravenously to such subject a blood plasma substitute comprising at least two water soluble polysaccharide oncotic agents one of which is eliminated from the circulation slowly and the other of which is eliminated from the circulation quickly buffered by lactate and optionally with sodium bicarbonate and supplemented with sodium chloride at physiological concentration.

DESCRIPTION OF THE INVENTION

The present invention comprises a mixture of components including at least one water soluble polysaccharide oncotic agent and preferably a mixture of two or more water soluble polysaccharide oncotic agents wherein one is capable of relatively quick elimination from the circulation and the other is capable of relatively slow elimination from the circulation. The mixture also generally includes sufficient sodium chloride to yield a physiologic concentration approximating that of human serum and sufficient calcium ion to yield a concentration in a range of 80 to 110 milligrams per liter.

In addition as an aqueous solution the forgoing mixture may also include magnesium ion in a concentration range which is less than 1 mEq and at least 0.5 mEq/l. Furthermore, optionally the forgoing mixture may include potassium ion at a concentration range of about 2 to 3 mEq/l. Both of the forgoing concentration ranges of magnesium ion and potassium ion are considered to be sub-physiologic for primates and especially human beings.

In greater detail, the present invention comprises a mixture of components which when placed in aqueous solution may be used to expand the plasma volume of a subject in need thereof. The forgoing components may be provided as a dry sterile mixture to which sterile diluent such as water, saline solution or dextrose solution may be added to form an aqueous solution. If provided as a dry sterile mixture, the materials may be provided in a sterile container suitable for mixture with sterile diluent such as sterile water, sterile saline or sterile dextrose solution. Alternatively the mixture of materials may be provided in a sterile container as an aqueous solution.

If the mixture of components according to the invention is provided as a dry sterile mixture suitable for fluid addition by a sterile saline solution, the amount of chloride salt of sodium in the dry mix is adjusted or omitted in amount equal to the sodium chloride contained in the sterile saline solution used. If the mixture according to the invention is provided as an aqueous solution, it is preferable to provide the solution as a sterile solution in a sterile container. Alternatively, the aqueous solution according to the invention may be provided as a non-sterile solution and may be subsequently sterile filtered into or autoclaved in sterile containers.

In another embodiment of the invention, the solution may be provided as a small volume sterile aqueous solution containing the mixture of components according to the invention in high concentration, which when mixed with a predetermined volume of an existing commercially available sterile oncotic solutions such as a commercial preparation of high molecular weight hydroxyethyl starch sold under the trade name Hespan (DuPont) or low molecular weight hydroxyethyl starch sold under the trade name Pentaspan (DuPont) provides a solution with the buffer or buffers and ions in the concentrations described herein in accordance with the invention.

For purposes of the further description of the invention, the mixture of components according to the invention will be discussed as an aqueous solution. From the following description of the invention it is expected that one ordinarily skilled in the art would be enabled to provide the mixture as a dry mixture and make the adjustments to amounts of sodium chloride and or dextrose as necessary to accommodate the amounts of sodium chloride found in normal saline solution for injection of a dextrose solution for injection, which may be used as a diluent for the dry mixture according to the invention.

The polysaccharide oncotic agents of the forgoing mixture of components are ones that are water soluble. By water soluble is meant that the polysaccharide will dissolve in water readily or with stirring or shaking. By water soluble oncotic agent is meant water soluble molecules which whendissolved in the fluid phase of circulating plasma in a living subject are of a size sufficient to prevent their immediate loss from the circulation by traversing the fenestration of the capillary bed into the interstitial spaces of the tissues of the body. The term polysaccharide oncotic agent thus does not include such polysaccharides as chitin since chitin is not soluble in water.

Polysaccharides that are water soluble and can act as oncotic agents are generally characterized as glucan polymers. In general, it is preferred that the water soluble polysaccharide oncotic agent is a glucan polymer that is non-antigenic.

Hetastarch which is a tradename for hydroxyethyl starch is a glucan polymer which can act as an artificial colloid when dissolved in water. Hydroxyethyl starch is derived from a waxy starch composed almost entirely of amylopectin with hydroxyethyl ether groups introduced into glucose units of the starch and the resultant material is hydrolysed to yield a product with a suitable molecular weight. The molar substitution of the hydroxyethyl moiety is 0.7 which means hydroxyethyl starch has 7 hydroxyethyl groups for every 10 glucose units. The average molecular weight of hydroxyethyl starch is 480,000 with a range of 400,000 to 550,000 and with 80% of the polymers falling in the range of 30,000 to 2,400,000. Hydroxyethyl groups are attached by ether linkage primarily at C2 of the glucose unit and to a lesser extent the C3 and C6 position. The glucose units are joined primarily in alpha (1–4) linkage with occasional 1–6 branches. The colloid properties of a 6% solution (wt/wt) of Hydroxyethyl starch approximates that of human serum albumin, with approximately 33% of a 500 ml intravenous dose eliminated in the urine after 24 hours. Approximately 10% of the dose remains circulating after 1 week. As used herein Hydroxyethyl starch is referred to as high molecular weight hydroxyethyl starch.

Pentastarch is another glucan polymer which can act as an artificial colloid when dissolved in water. Pentastarch is also derived from a waxy starch composed almost entirely of amylopectin with hydroxyethyl ether groups introduced into glucose units of the starch and the resultant material is hydrolysed to yield a product with a suitable molecular weight. The molar substitution of the hydroxyethyl moiety is 0.45 which means pentastarch has 45 hydroxyethyl groups for every 100 glucose units. The average molecular weight of pentastarch is approximately 264,000 with a range of 150,000 to 350,000 and with 80% of the polymers falling in the range of 10,000 to 2,000,000. Hydroxyethyl groups are attached by ether linkage primarily at C2 of the glucose unit and to a lesser extent the C3 and C6 position. The glucose units are joined primarily in alpha (1–4) linkage with occasional 1–6 branches. As used herein pentastarch is referred to as low molecular weight hydroxyethyl starch.

Other polysaccharide derivatives may be suitable as oncotic agents in the solutions according to the invention including hydroxymethyl alpha substituted (1–4) or (1–6) polymers. Cyclodextrins such as hydroxypropyl substituted β or γ cyclodextrin may be suitable as oncotic agents in the blood substitute according to the invention.

D-glucose polymers that are soluble in water may also be used as the water polysaccharide oncotic agent in the mixture according to the invention. Examples of such D-glucose polymers are Dextran, which is D-glucose linked predominantly in alpha (1–6) linkage, Dextran in a molecular weight range of 30,000 to 50,000 daltons (D) are preferred. Most preferred is Dextran 40 having a molecular weight of about 40,000 D.

The concentration of the polysaccharide oncotic agent in the solution according to the invention will be sufficient so that a significant amount of the oncotic agent is still circulating in a subject 2 to 5 days after administration of the solution. Accordingly, the solution according to the invention will have a mixture of high molecular weight and low molecular weight poly- saccharide oncotic agents the relative amounts of which have been optimized to achieve this effect in this time period. The solution according to the invention will preferably contain a lower or equal concentration of higher molecular weight polysaccharide oncotic agents as compared to the concentration of lower molecular weight polysaccharide oncotic agents. Higher molecular weight polysaccharide oncotic agents such as high molecular weight hydroxyethyl starch and dextran 70 are generally eliminated from the circulation at a slower rate than lower molecular weight polysaccharide oncotic agents such as low molecular weight hydroxyethyl starch and dextran 40. High molecular weight hydroxyethyl starch is eliminated from the circulation of a human being slowly. Approximately 33% of a 500 ml infusion of 6% high molecular weight hydroxyethyl starch is eliminated from the circulation after 24 hours, with approximately 10% of the dose remaining in the circulation after 2 weeks. Low molecular weight hydroxyethyl starch is eliminated from the circulation of a human being quickly. Approximately 70% of a 500 ml infusion of 10% low molecular weight hydroxyethyl starch is eliminated from the circulation after 24 hours, with approximately 20% of the dose remaining in the circulation after 1 week. Elimination time for 6% dextran 40 and similar low molecular weight water soluble polysaccharide oncotic agents are similar.

When Dextran 40 or low molecular weight hydroxyethyl starch is used in the solution according to the invention its concentration is in a range of 6.0 to 8.5%. A solution comprising about 8% Dextran 40 (wt/wt) or about 80 grams (g) per liter (l) of water is generally used. When Dextran 70 or high molecular weight hydroxyethyl starch is used in the solution according to the invention its concentration is in a range of 5.5% to 6.5%. A solution comprising about 6% high molecular weight hydroxyethyl starch (wt/wt) or about 60 grams (g) per liter (l) of water is generally used.

When it is necessary to treat a subject who has lost a significant amount of blood, generally up to about 30% to 40% of blood volume with a plasma expander, the forgoing mixture may be administered intravenously as a sterile aqueous solution. In another embodiment of the invention, the oncotic agent is a mixture of high molecular weight water soluble polysaccharide, such as high molecular weight hydroxyethyl starch or dextran 70, and low molecular weight water soluble polysaccharide, such as low molecular weight hydroxyethyl starch or dextran 40. In this embodiment of the invention which may be particularly useful when it is not possible to transfuse a subject with whole blood quickly, the amount of high and low molecular weight hydroxyethyl starch is adjusted to initially stabilize the colloid osmotic pressure of the subject's blood and then to gradually remove the water soluble oncotic agent as the patient begins to replenish circulating serum proteins.

Solutions according to the invention having this composition will typically include high molecular weight hydroxyethyl starch in a range of from 5 to 40 grams per liter and dextran 40 or low molecular weight hydroxyethyl starch in a concentration of 20 to 75 grams per liter; however the concentration of the two water soluble oncotic agents together will generally not exceed 80 grams per liter. It is believed that a solution comprising about 20 grams per liter high molecular weight hydroxyethyl starch and about 50 grams per liter of dextran 40 or about 50 grams per liter of low molecular weigh hydroxyethyl starch is desirable. A solution comprised of about 30 grams per liter high molecular weight hydroxyethyl starch and about 30 grams per liter of dextran 40 or about 30 grams per liter of low molecular weight hydroxyethyl starch may be preferred.

In determining the amount of the two oncotic agents in the solution according to the invention, the amounts of the two agents are adjusted to maintain oncotic balance without infusing so much of the oncotic agent that the plasma becomes hyperoncotic and circulating serum proteins are removed from the circulation by hepatic absorption or renal excretion or other physiological mechanisms. Thus it is important that the high molecular weight hydroxyethyl starch or dextran 70 and low molecular weight hydroxyethyl starch or dextran 40 should not together exceed about 8% weight/volume percent. Solutions exceeding this concentration of oncotic agent may be physiologically hyperoncotic leading either to removal of serum protein from the circulation or an inhibition of their production. Since high molecular weight hydroxyethyl starch and dextran 70 are not quickly eliminated from the circulation the amount of these oncotic agents will generally not be more than 75% of the total weight of the water soluble oncotic agents in the solution. By using a high molecular weight oncotic agent in the solution in combination with a low molecular weight solution, the addition of the solution to a subject's circulation either as a plasma expander after trauma or surgery, or as a blood substitute when more than 30% of the subject's circulating volume is made up of the blood substitute, the subject's circulating oncotic pressure is quickly stabilized, fluid exchange between the circulating blood compartment and the interstitial spaces is minimized, and edema is curtailed. Furthermore, the rate of elimination of the low molecular weight oncotic agent is sufficiently quick that oncotic balance can be maintained without inhibiting the subject's production of new serum proteins, while at the same time the rate of elimination of the high molecular weight oncotic agent is sufficiently slow that the polysaccharide oncotic agent is able to maintain oncotic balance until sufficient protein has been produced after substantially complete elimination of the low molecular weight polysaccharide oncotic agent.

The solutions according to the invention with calcium and magnesium ions provided by the solution have the advantage of providing essential ions required for the patient's blood to maintain its ability to clot. This advantage may be significant to a patient suffering from a hemorrhage or internal bleeding with concomitant loss of blood pressure due to decreased blood volume. In these patients the administration of conventional plasma expanders such as Hespan, Pentaspan, Macrodex and Rheomacrodex may lead to dilution of blood plasma proteins and ions essential to the formation of blood clots which may be life saving particularly for trauma patients. If the conventional plasma expanders are used, dilution of the blood proteins and electrolytes essential for clotting may have fatal consequences. By administering the solution according to the invention, the provision of essential electrolytes will lead to a greater preservation of the ability of the patient's blood to clot if necessary.

In the solution according to the invention the magnesium ion concentration will range between 0.5 and 0.9 mEq/l. Magnesium ion is generally sequestered intracellularly in an intact mammalian subject; however in the event of trauma which damages tissues, magnesium ion concentration will increase. Thus it is desirable to administer the solution according to the invention with magnesium ion concentrations on the low end of this range when tissue damage has occurred. Typically this will be in situations wherein the solution is administered to maintain the blood volume of a trauma victim. By contrast, when the solution is used to substitute for the blood of a subject, such as when surgical procedures at low temperature are carried out, it is desirable to administer the solution according to the invention with magnesium ion concentrations at the high end of the range. In either case the concentration of the electrolyte magnesium ion is one that is generally considered to be less than physiological. When a subject's blood magnesium ion concentration falls below normal several problems may occur including tetany and irregular heartbeat. In maintaining electrolyte levels in normal human subjects, magnesium ion concentration of less than 0.5 mEq/l are considered to be "panic levels" ie.—concentrations which require immediate intervention and administration of available high concentration magnesium ion containing solutions to normalize the magnesium ion concentration. The normal physiological range for magnesium ion in blood is generally considered to be 1–2 mEq/l. Thus the solutions according to the invention unexpectedly use magnesium ion concentrations that are less than physiological to maintain subject blood volume or blood substitution at low temperature. This is unlike the teaching of prior teachings such as U.S. Pat. Nos. 4,923,442 and 5,130,230 and standard nursing texts on maintenance of proper electrolyte balance.

It has been discovered that the utility of the forgoing solutions which may be used as plasma volume expanders, may be extended by also including a sufficient amount of a water soluble preparation or aqueous colloid suspension of vitamin K to stimulate the liver to produce blood serum proteins essential to maintaining normal blood clotting function, usually expressed as the time it takes for a standard volume of whole blood or blood plasma to clot. In general, a concentration of vitamin K in the solution sufficient to deliver about 5 to 10 mg of vitamin K to the subject is required in the solution according to the invention. Thus if 2–3 liters of solution are delivered to the patient's circulation a concentration of 2 to 3 mg of vitamin K per liter will be used. It is believed that a concentration of about 2.5 mg vitamin K is optimal for this purpose.

The foregoing solutions may also be augmented, optionally, by a small amount of potassium ion generally in a concentration range between 2 to 3 mEq/l. The use of potassium ion in this concentration range may be indicated in individuals who have lost a substantial amount of blood but who have not been subject to extensive tissue trauma or whole blood transfusion. In both of these latter conditions, significant amounts of potassium ion may be released into the blood stream by lysis of blood cells or tissue cells. If high concentrations of potassium ion released by such trauma or transfusion prevail in the blood for a significant period of time, particularly as a result of lowered renal perfusion and filtration rates because of low blood volume, it may be desirable to omit potassium ion from the solution administered to such patients. On the other hand if normal potassium concentrations are present in the subject's remaining circulating blood, it will be desirable to include potassium in the solution according to the invention.

One of the problems in treatment of hypovolemic patients who have lost substantial amounts of blood, generally greater than 30% of their normal blood volume, is the need to provide in addition to essential electrolytes, and reasonable oncotic balance, sufficient ability to maintain pH and nutrition of the central nervous system, while at the same time permitting the remaining blood in the subject to function normally. Patients who have lost 30% or greater of their blood volume and who are treated with Hespan® frequently experience breaking of their red blood cells or hemolysis in addition to other problems associated with extreme hemodilution such as reduced clotting time and prothrombin levels.

In individuals who have lost more than 30% of their blood it is desirable to further augment the forgoing solutions as described further herein below with respect to buffering capacity to maintain proper pH, assimilable sugar and, particularly when it is difficult to find a matching blood donor or whole blood transfusion would be otherwise difficult, a material which stimulates the formation of blood proteins necessary for proper blood clotting. In particular Vitamin K in a form which may be administered in aqueous solution is included at a concentration effective to stimulate hepatic synthesis of blood coagulation factors including prothrombin (factor II) proconvertin (factor VII), thromboplastin (factor I) and Stuart factor (factor X).

To provide buffering capacity the forgoing solution will include a sufficient amount of buffer to permit effective buffering of the circulating blood in a pH range around 7.4. In some uses, the buffer is sodium lactate at a concentration in a range of 10 to 30 mM, preferably about 28 mM. Sodium lactate is preferred because lactate is a compound naturally occurring in the body. Additionally, other suitable buffers usable in lieu of lactate are small organic acid ions that may be metabolized such as acetate, pyruvate, gluconate and succinate. Citrate should not be used since it adversely affects the ability of whole blood to clot. $NaHCO_3$ (sodium bicarbonate) will be provided as a buffer inaddition to sodium lactate, in a concentration of about 5 to 10 milliMolar (mM). It is also possible to use a biological buffer such as HEPES or a balanced solution of Trizma base and Trizma HCl in lieu of lactate or bicarbonate. When Trisma base/Trizma HCl is used to provide buffering, these components are added in the amount of about 0.83 and 2.86 grams per liter of solution respectively; however biological buffers are preferably not used unless the oncotic agent is provided by a mixture of water soluble high and low molecular weight polysaccharides.

Vitamin K which is compatible with aqueous media for injection will be preferred in the solution according to the invention. Preparations of this general type are known and are sold as pharmaceutical preparations in their own right under various names such as menadiol sodium diphosphate, which is a synthetic water-soluble derivative of menadione vitamin K3 (Roche, Nutley N.J.) and phytonadione which is a clear aqueous dispersion of vitamin K.sub.1 (Merck Sharp & Dohme). In general the concentration of aqueous vitamin K in the solution according to the invention will be sufficient to deliver between 5 to 10 milligrams to the subject. The wide range of vitamin K concentration is necessary to accommodate patients in age and weight from infant to adult.

The solution according to the invention for administration to patients who have lost more than 30% of their blood volume will also include an easily assimilable sugar. In general dextrose (glucose) is preferred in a concentration sufficient to sustain nutrition parenterally. In general a concentration of about 5 mM glucose will be used.

When used as a blood plasma expander in a hypovolemic subject, the solution according to the invention will be administered in an amount up to about 30% of the average blood volume of an average subject. If the subject is the size of an average adult male human being the average blood volume is about 5000 ml and the volume of the solution according to the invention will be up to about 1500 ml. The composition of the solution according to the invention used as a blood plasma expander will generally comprise an aqueous solution of water soluble polysaccharide oncotic agent, with dissolved Sodium chloride at physiologic concentration (about 0.9% or 154 mM), calcium chloride at a concentration of about 2.5 mM and optionally magnesium chloride in a concentration range which is less than 1 mEq/l and at least 0.5 mEq/l In general a magnesium chloride concentration of about 0.475 mM is preferred. The water soluble polysaccharide may be high molecular weight hydroxyethyl starch dextran 70 or dextran 40 in a concentration of about 60 grams/liter. Optionally, the forgoing mixture may include potassium ion at a concentration range of about 2 to 3 mEq/l. In an additional option the solution may also include aqueous vitamin K in a concentration sufficient to deliver between 5 to 10 milligrams to the subject. When administered to a subject the solution according to the invention will be administered intravenously as a sterile solution by a continuous fast infusion.

When used as a blood replacement in a severely hypovolemic subject or when used in a procedure in which the subject blood is deliberately removed, the solution will be administered as a sterile solution in an amount exceeding 30% of the average blood volume and will generally exceed 1500 ml. The composition of the solution according to the invention used as a blood replacement will generally comprise the components in the amounts described in the preceding paragraph. If administered to a mammalian subject that has been chilled to hypothermic body temperatures, (generally 5 or more degrees Centigrade below normal body temperature) potassium ion may be completely omitted from the solution or may be present in sub-physiological amounts up to about 3 mEq/l according to the invention. If the solution is administered to a subject that is at normal body temperature, the solution according to the invention may include potassium ion at a concentration range of about 2 to 3 mEq/l.

In addition, whether administered as a blood replacement to a hypothermic subject or a subject at normal temperature, the solution will also contain a buffer. A preferred buffer is lactate at a concentration of about 28 mM. Sodium lactate is preferred because lactate is a compound naturally occurring in the body. Alternatively, the buffer will also include a sufficient amount of $NaHCO_3$ to permit effective buffering of the circulating blood in a pH range around 7.4. In general, $NaHCO_3$ will be provided in a concentration of about 5 to 10 milliMolar (mM), and preferably at about 5 mM particularly if the subject's body temperature is 5 degrees Centigrade below normal when the solution is administered as a blood plasma substitute or blood plasma expander.

Prior art blood substitute solutions generally teach that it is desirable to provide a buffer that is a biological buffer in a solution having, prior to administration to a subject, a pH range of about 7.2 to 7.8. Such buffers are exemplified by HEPES, MOPS, TRIS, and other similar buffering salts. Such biological buffers are very expensive, in contrast to the cost of the components in the solutions according to the invention. The buffering capacity of these biological buffers is greatest in the pH range 7.2 to 7.8 which is the pH range in which mammalian subjects normally regulate blood pH. One great disadvantage of these biological buffers is that, although they buffer best at normal physiological pH in vitro, most are as yet not generally regarded as safe for human administration and none has been used clinically as an integrated component in a large volume parenteral solution. By contrast, it has been surprisingly found by the inventors that small organic acid salts such as sodium lactate and sodium bicarbonate can be used as buffers in the plasma extender and blood plasma substitute solutions according to the invention even though the pH of these solutions prior to administration are not physiological. In the case of lactate alone, the average pH is about 5.5 prior to administration. In the case of bicarbonate as buffer, the solutions according to the invention have a pH greater than pH 8 at room temperature prior to administration.

The use of these small organic acid salts as buffering agents in the solutions according to the invention is particularly advantageous when the solution is used to substitute a significant amount of a subject's missing blood volume. Thus the use of small organic acid salts as buffers in the solutions of the invention is particularly advantageous when the solution is used to replace or substitute for blood volumes in excess of 30% of the subjects normal circulating blood volume. By using small organic acid salts as buffers, such as sodium lactate or sodium bicarbonate, it is possible to perfuse a subject for many hours using the solutions according to the invention without encountering the hazard of uptake and sequestration of chemical compounds such as HEPES, MOPS, TRIS and other similar buffering salts used in prior art solutions such as those disclosed in Segall et al., U.S. Pat. Nos. 4,923,442 and 5,130,230. Unexpectedly, it has been found that despite an initial pre-administration pH of about 5.5, the solutions according to the invention in both primate and rodent models are able to maintain pH of the blood after infusion of 7.2 to 7.8 even when used to substantially and completely replace all of the circulating blood of a subject.

In a further embodiment of the invention, Applicants have discovered that the small molecule organic acid salt is preferably sodium lactate in a concentration sufficient to maintain the solution at a pH of about 5.5 prior to administration, provided that the volume of blood to be replaced is no greater than about 30% of the blood volume and is administered at normal mammalian body temperatures. It is also preferred to supplement the lactate as buffer in the solution with sodium bicarbonate when the solution is used to substitute more than 30 percent of the subject's blood volume, particularly if this substitution is carried out under conditions wherein the subject is maintained at temperatures between 7 degrees centigrade below normal temperature and about 1 degree centigrade.

This discovery is particularly important when one is using the solution to maintain a subject during procedures in which the subject is cooled to core body temperatures at which the subject is not itself capable of maintaining normal physiological homeostatic mechanisms such as those which maintain blood pH between 7.5 and 7.8. Lactate infused initially in the solution according to the invention, does not have sufficient buffering capacity at low temperature. Therefore, in using the solution according to the invention to substitute the blood of a subject under cold hypothermic conditions, it is advantageous to use the solution containing sodium lactate to initially substitute for the subject's blood, and as the subject's blood is replaced to begin substitution using sodium bicarbonate in addition to sodium lactate since sodium bicarbonate has a greater buffering capacity. Thus, complete substitution may be accomplished using a system of two solutions, the initial solution comprising sodium lactate as buffer and the subsequent solution using sodium bicarbonate and sodium lactate.

When used as a plasma extender, which in general is in situations where 30% or less of the subject's normal blood volume is being added (usually after blood loss due to trauma or surgery), the solution according to the invention will usually be administered to a subject at normal body temperature for that mammalian subject. It is preferred that the solution according to the invention, when used as a plasma extender and administered at about normal body temperature, have only lactate as a buffer, which is provided in the solution as sodium lactate. At normal body temperatures, lactate may be eventually metabolized by the subject leaving assimilable (or easily excreted) sodium ion.

When used as a plasma substitute, which in general is in situations where more than 30% of the subject's normal blood volume is being perfused into the subject, usually when the subject's blood is being removed at the same time as the solution according to the invention is administered, the solution according to the invention will usually be administered to a subject that has been chilled to a body temperature below normal, usually 7° C. or more below the normal temperature for that mammalian subject. It is preferred that the solution according to the invention, when used as a plasma substitute and administered at such sub-normal body temperatures, have in addition to lactate as a buffer, sodium bicarbonate ($NaHCO_3$). In practice, if the process of replacing the subject's blood is started before the subject's body temperature is substantially below normal, the solution according to the invention with only sodium lactate as buffer will be administered. As body temperature falls below normal the solution according to the invention with sodium lactate and sodium bicarbonate will be administered to the subject. Furthermore, during the period of time that the subject is maintained at below normal temperature, it will be periodically perfused with fresh solution according to the invention containing both sodium lactate and sodium bicarbonate as buffer. The solution according to the invention containing both sodium lactate buffer and sodium bicarbonate solution is preferred when the subject is to be used for the purpose of harvesting body organs for eventual transplant and organ preservation is of paramount importance. In addition this same solution may be used to perform surgery on a subject when it is necessary to reduce the subject's temperature to slow metabolic activity and the removal of blood is required to optimize the condition of the surgical field.

In one embodiment of the invention 0.9% saline, Ringer's lactate, Plasmalyte, Normasol or other commonly used crystalloid solution can be used to replace up to 50% of the subject's blood instead of the lactate-buffered solution. This solution is then rapidly replaced by the lactate and bicarbonate buffered form of the invention.

The solutions according to the invention containing lactate have an initial pH prior to administration to a subject of about 4 to 5.5. It is possible to more easily terminally heat sterilize the solutions according to the invention at pH 5.5, without adversely affecting the status of the polysaccharide oncotic agents which tend to caramelize when terminally sterilized at pH exceeding 7.0. Sodium bicarbonate may limit the ability of the solution to be terminally heat sterilized. To facilitate use of the solutions according to the invention the solution may be supplied as a kit including a terminally heat sterilized solution including all the components of the solution according to the invention in a ready to use container except sodium bicarbonate and a second sterile container of pre-measured sterile sodium bicarbonate solution which may be added using sterile technique to the ready to use solution.

Less preferred buffer in the solutions according to the invention is a biological buffer such as Hepes or a balanced solution of Trizma base and Trizma HCl in lieu of Bicarbonate. When Trizma base/Trizma HCl is used to provide buffering, these components are added in the amount of about 0.83 and 2.86 grams per liter of solution respectively and are preferably used only when the water soluble polysaccharide oncotic agent is a combination of high molecular weight and low molecular weight polysaccharides.

Also included in the solution according to the invention when administered as a blood replacement, the solution will include an assimilable sugar, preferably dextrose at a concentration of about 5 mM. When administered as a blood replacement, the solution may be quickly infused through a venous cannula or other indwelling device able to permit large volume infusion. The blood pressure of the subject may be monitored so that central venous pressure remains below 10 millimeters of mercury. If pressure begins to increase, a volume of blood may be removed through the venous cannula and the pressure equilibrated at an acceptable level. If desired the solution according to the invention may be perfused into the subject by means of a pump and closed circuit including a reservoir of the solution according to the invention until the subject's blood is partially or fully replaced with the solution according to the invention as desired.

The invention will be better understood in connection with the following examples which are intended by the inventors to be illustrative of the invention but not limiting.

EXPERIMENTAL

EXAMPLE I

Reviving An Ice-Cold Blood-Substituted Baboon After Chilling To Near-Freezing

A 7 kg male baboon of the species Papio anubias was chilled and blood-substituted to a minimum deep esophageal temperature of 2° C. After reaching that temperature, the animal was warmed, revived and recovered.

The baboon was injected i.m. with ketamine. A catheter was inserted in the right cephalic vein, and 2.5% pentothal injected i.v. The primate was then fitted with an endotracheal tube and placed on flether anesthetic. The animal was shaved, and a Ringer's lactate drip initiated i.v., with its rate titrated to the animal's arterial blood pressure. The right femoral artery was catheterized to allow for blood pressure monitoring, and a 3-way stopcock placed in-line to allow arterial blood sampling every 10–60 minutes throughout the entire procedure. A wedge catheter was implanted in the pulmonary artery through the right radial vein.

The extracorporeal circuit was constructed with a hard shell venous reservoir, Biomedicus pump head, hollow fiber membrane oxygenator with integral heat exchanger, flow meter and a secondary in-line heat exchanger added as close to the animal as possible. The circuit incorporates a section between the outflow cannula and the venous reservoir to remove effluent and a 1 L funnel/reservoir to quickly refill the venous reservoir with blood substitute or blood. A cooler to supply the oxygenator's built-in heat exchanger and the secondary heat exchanger with circulating ice water (and warm water) was required. All tubing in contact with blood or blood substitute was sterile. The venous reservoir and circuit was filled with 2 liters of HL solution.

A catheter was placed in the left brachial vein to allow monitoring of central venous pressure (CVP). Arterial blood gases, pH, $K^+$ and hematocrit are measured in each sample, and in some cases, electrolytes, and enzymes as well.

Venous outflow cannulas were placed in the left femoral vein. An arterial inflow cannula was placed in the left femoral artery. After the venous cannula was implanted, heparin was injected iv. SoluMedrol (12 mg/kg) was then injected iv and the eyes coated with a protective ointment. An esophageal tube was inserted, and Maalox administered. The esophageal tube was fitted with a temperature probe for recording deep esophageal temperature. The EKG leads are put in place and the animal was immersed in crushed ice.

Following the onset of cooling, the animal was managed anesthetically light with 2.5% pentothal (at doses between 1–3 cc). When body temperature reaches 30° C., 200 ml of the solution indicated below designated HL was infused in the brachial vein and an equal amount of blood was drained from the arterial cannula and collected sterile for later use. When body temperature dropped below 29° C., anesthetic was discontinued. After chilling to 25° C., the animal was placed on bypass. At that time, the clamps are released which isolate the baboon's circulation from the bypass circuit, and an amount of HL solution sufficient to flush substantially all of the animals blood (for the 7 kg baboon approximately 2 liters of solution) was allowed to blood-substitute the animal, and whole and diluted blood was removed as venous effluent and saved for revival. Following this, its heart was arrested by the intra-arterial administration of 2M KCl added via the secondary heat exchanger.

After the heart was arrested, the solution indicated below designated HLB was added to the reservoir and circulated into the animal. As this solution perfused into the animal, a blood-blood plasma-substitute mixture was continuously removed as a venous effluent until the HLB solution replaced the initial circulating solution. The temperature was then dropped to 2° C. as rapidly as possible, while maintaining CVP and wedge pressures at acceptable values. Rewarming then began. During this period, HLB solution was periodically drained from the animal's circulation while adding new HLB solution to the perfusion apparatus.

The animal was warmed keeping the CVP below 5 mm Hg. When the esophageal temperature reached 15° C., the animal's own whole blood collected during cooling was added to the circuit, replacing the HLB solution. Following this, enough donor whole blood was added to raise the hematocrit above 20%.

Heartbeat resumed when the body temperature rose. As the temperature rose, the hematocrit was elevated until it reached normal between 25–35%. As the temperature climbed above 25° C. Lasix was injected iv. Over the next hour, the baboon was warmed. Ventilation was initiated, and the baboon's body temperature rose to 37° C. A dopamine i.v. drip was begun when body temperature reached 25° C. As the baboon was warmed further, the dopamine drip was increased, and then, as blood pressure climbed, it was reduced, and then discontinued. The animal was removed from bypass, the catheters and cannulas pulled, and incisions closed. Sodium bicarbonate was administered iv. as needed to manage acidosis. After revival, the animal was weaned from the ventilator.

The circulating fluid was sampled periodically from the right femoral artery and the pH, electrolyte levels and hematocrit were determined and are reported in Table I. Solution Compositions (in mM Concentrations Except HES [g/l])

| Solution | HES | NaCL | MgCl | CaCl$_2$ | Glucose | NaLactate |
|---|---|---|---|---|---|---|
| HL | 60 | 115 | 0.25 | 2.5 | 5 | 28 |

HLB has the same composition as HL but includes in addition 5 mM NaHCO$_3$. HES is high molecular weight hydroxyethyl starch.

TABLE I

| Sample | Elapse time | pH | Ca++ | K+ | HCT* |
|---|---|---|---|---|---|
| 1 | 0:00 | 7.654 | 9.3 | 3.1 | 40 |
| 2 | 0:15 | 7.646 | | | |
| 3 | 0:31 | 7.555 | | | |
| 4 | 0:58 | 7.536 | 8.9 | 2.7 | 39 |
| 5 | 1:13 | 7.627 | 8.9 | 3.2 | 25 |
| 6 | 1:40 | 7.340 | | < | <0.5 |
| 7 | 1:47 | 7.201 | | < | 0.5 |
| 8 | 1;56 | 7.455 | | 2.4 | 0.25 |
| 9 | 2:09 | 7.326 | | | 0.25 |
| 10 | 3:01 | 7.468 | 10.4 | 3.2 | |
| 11 | 3:53 | 7.498 | 10.5 | 2.9 | |
| 12 | 4:11 | 7.657 | 9.5 | 3.9 | 5.0 |
| 13 | 4:18 | 7.439 | 6.7 | 5.9 | 22 |
| 14 | 4:35 | 7.593 | 8.9 | 4.3 | 13 |
| 15 | 5:02 | 7.380 | 8.0 | 3.2 | 23 |
| 16 | 5:23 | 7.285 | 8.8 | 2.7 | 26 |
| 17 | 5:41 | 7.110 | 9.2 | 3.1 | 32 |
| 18 | 6:07 | | 9.0 | 4.4 | 36 |
| 19 | 6:11 | 7.038 | 7.8 | 3.8 | 34 |
| 20 | 6:32 | 7.284 | | 3.3 | 32 |
| 21 | 6:57 | 7.437 | | | |

HCT = Hematocrit

EXAMPLE II
Reviving A Hamster After Ice-Cold Blood Substitution

In this experiment an 80 g female hamster was revived after chilling below 4° C. The animal was anesthetized by i.m. injection of ketamine and surrounded in crushed ice. When its body temperature reached 12°–16° C., it was removed from the ice and placed on a surgical stage. Its right femoral vein was cannulated with a modified 24 gauge angiocath, and its right femoral artery was cannulated with a microcannula.

The micro-cannula was attached to a line which was also connected to a reservoir and a pump, and the reservoir was chilled in crushed ice and contained ice-cold hypothermic blood substitute solution described in example I as HL. The animal was ventilated with 100% O$_2$ and perfused with 7 ml of blood substitute solution (150% of its estimated blood volume), until its hematocrit fell to 6%, its heart was stopped with an i.v. injection of 0.15 ml of 1M KCl During the perfusion, the blood substitute, whose initial pH was 5.5, comprised much of the venous effluent. The pH of the venous effluent first fell from 7.35 to 7.23, and then rose to 7.41, and later 7.55.

After 35 minutes of perfusion with ice-cold blood substitution perfusion was stopped and the animal maintained at the ice-point. After 30 minutes, whole blood was infused into the femoral artery, and blood substitute removed as a venous effluent.

The animal's heartbeat recovered after 25 minutes of blood substitution and the hematocrit reached 48% within another 10 minutes, and perfusion was halted. Five minutes later, breathing began. Within 20 minutes the animal was awake, and within one hour, it regained normal posture and was able to move about its cage. This recovery was the quickest ever observed using ice-cold blood substitution. The animal survived without complications for at least one week after the experiment and appeared normal.

The experiment confirmed the utility of the present formulation for use in ice-cold blood substitution. The solution containing sodium lactate initially has a pH of between 4 and 6, but after the lactate is metabolized, the resulting venous effluent has an alkaline pH, which can counteract acidity which may develop during rewarming. Also, there is some evidence accumulating that hypothermia can cause leakage of blood proteins out of the circulation, and into tissue, creating edema. The new formulation contains high molecular weight hydroxyethyl starch which has an average molecular weight of 480,000, and is therefore less likely to leak out of the vasculature than albumin, found in blood, or dextran 40.

EXAMPLE III
HL solution As An Artificial Plasma

A 80 g female hamster was injected im with an anesthetic mixture of ketamine, xylazine and acepromazine, and its right femoral vein and artery were cannulated as described in Example II. The animal was perfused with the artificial plasma solution. designated HL in Example I containing however 2 mM K+, until its femoral venous blood had a hematocrit of 18%. An equal amount of venous effluent was removed as the artificial plasma solution was infused into the femoral artery.

The catheters were removed and the incisions closed. The animal recovered from the anesthesia and survives at this writing, one week after the experiment. Since the initial hematocrit was 48%, dilution of the blood to 18/48 of its initial concentration represents a blood substitution of 62.5%.

EXAMPLE IV
Effect of Perfusate Composition on pH

Hamsters were injected i.m. with an anesthetic ketamine. After they were anethesized they were placed in crushed ice.

When body temperature cooled to about 12.degree. C. as measured by a rectal thermocouple, the hamsters were placed on a surgical stage. The carotid artery and jugular vein were exposed and cannulas were inserted into each. Body temperature was lowered further to below 5 degrees centigrade and using a peristaltic pump perfusate was pumped into the artery at about 0.3 ml per minute while venous effluent was collected and the pH of the effluent solution measured.

The perfusate solution consisted of the following constituents:

| | | |
|---|---|---|
| High molecular weight hydroxyethyl starch | 0.06 | grams/ml |
| Sodium chloride | 115 | mM |
| Magnesium chloride | 0.25 | mM |
| Calcium chloride | 2.5 | mM |
| Glucose | 5 | mM |

A) Using the perfusate indicated above including 28 mM sodium lactate, having an initial pH 6.0 at room temperature (r.t.), the following pHs were obtained for samples of the effluent solutions:

| volume (ml) out | pH |
|---|---|
| 1 | 7.3 |
| 2 | 7.2 |
| 5 | 7.0 |
| 20 | 6.9 |

Effluent samples were combined and the pH measured. The pH of the combined samples was 7.0.

B) Using the perfusate indicated above including Tris buffer (25 mM, having an initial pH 7.8 r.t., the following pHs were obtained for samples of the effluent solutions:

| volume (ml) out | pH |
|---|---|
| 1 | 7.3 |
| 2 | 7.25 |
| 4 | 7.28 |
| 8 | 7.3 |
| 11 | 7.16 |
| 20 | 7.2 |

Effluent samples were combined and the pH measured. The pH of the combined samples was 7.2.

C) Using the perfusate indicated above including 28 mM sodium lactate and 10 mM sodium bicarbonate, having an initial pH 8.3 r.t., the following pHs were obtained for samples of the effluent solutions:

| volume (ml) out | pH |
|---|---|
| 1 | 7.3 |
| 2 | 7.2 |
| 5 | 7.32 |
| 8 | 7.41 |
| 12 | 7.53 |
| 20 | 7.55 |

Effluent samples were combined and the pH measured. The pH of the combined samples was 7.5.

D) Using the perfusate indicated above including 28 mM sodium lactate and 5 mM sodium bicarbonate, having an initial pH 8.2 r.t., the following pHs were obtained for samples of the effluent solutions:

| volume (ml) out | pH |
|---|---|
| 1 | 7.3 |
| 3 | 7.28 |
| 6 | 7.35 |
| 8 | 7.33 |
| 10 | 7.38 |
| 12 | 7.50 |
| 15 | 7.53 |
| 20 | 7.51 |

Effluent samples were combined and the pH measured. The pH of the combined samples was 7.5.

E) Using 2 solution system in which the solutions had the following compositions:
1) the perfusate indicated above including 28 mM sodium lactate having an initial pH 6.0 r.t.; and 2) the perfusate indicated above including 28 mM sodium lactate and 5 mM sodium bicarbonate, having an initial pH 8.2 r.t.

The following pHs were obtained for the samples of the effluent solutions:

| volume out | pH |
|---|---|
| With 1: | |
| 1 | 7.25 |
| 4 | 7.13 |
| 8 | 7.11 |
| Switch to 2: | |
| 10 | 7.41 |
| 14 | 7.44 |
| 17 | 7.45 |
| 20 | 7.49 |
| 23 | 7.4 |

Effluent samples of ml 10–23 were combined and the pH measured. The pH of the combined sample was 7.41.

This series of experiments show that the addition of only 5 mM sodium bicarbonate to the lactate-buffered perfusate solution is sufficient to maintain near normal pH during total body washout at ice-cold temperatures. Interestingly and unexpectedly the lactate/bicarbonate buffer system is superior to biological buffers such as Tris when flushing animals with large volumes of solution at cold temperatures. Using the biologic buffers pH generally falls well below normal. Using only lactate the pH falls to an even lower pH (however use of lactate only when perfusing warm metabolically active animals, results in normal to basic pH). Using lactate with the addition of a small amount of bicarbonate, provided venous effluent with a near normal pH It was particularly surprising that such a small amount of bicarbonate added to the solution could maintain adequate pH of venous effluent when perfusing large volumes.

It will be apparent from the foregoing that the blood plasma substitute solutions described herein may also be used to increase the circulating fluid volume of a hypovolemic subject. If used for this purpose, as described above, the concentration of the water soluble oncotic agent wherein the blood plasma substitute solution comprises a single oncotic agent will have the same concentration ranges as the plasma expander solutions. Thus for example when Dextran 40 or low molecular weight hydroxyethyl starch is used in the solution according to the invention its concentration is in a range of 6.0 to 8.5%. A solution comprising about 8% Dextran 40 (wt/wt) or about 80 grams (g) per liter (l) of water is generally used. When Dextran 70 or high molecular weight hydroxyethyl starch is used in the solution according to the invention its concentration is in a range of 5.5% to 6.5%. A solution comprising about 6% high molecular weight hydroxyethyl starch (wt/wt) or about 60 grams (g) per liter (l) of water is generally used.

The new solutions according to the invention will be readily seen to confer several advantages over existing blood substitute solutions. Since the new formulation contains no biological buffer, no unphysiological components are present. All of the ingredients in the formula occur naturally in living mammals in significant quantities. Furthermore, the low pH of this formulation allows it to be terminally sterilized more readily. The components, being naturally occurring compounds omnipresent in significant quantities are inexpensive, and can therefore be produced at less cost. Since the formulation has a slightly acid pH, it has storage advantages as well.

What is claimed is:

1. A method for increasing the circulating volume of a hypovolemic subject comprising administering to said subject a plasma-like substance comprising an aqueous solution of at least one hydroxyethyl starch selected from the group consisting of a hydroxyethyl starch having an average molecular weight of 400,000 to 550,000 daltons and a hydroxyethyl starch having an average molecular weight of 150,000 to 350,000 daltons and an organic acid salt; wherein
   said solution has at least one of the following characteristics:
   is terminally heat sterilized; and
   has a pH between 4 and 6.5.

2. The method according to claim 1, wherein said hydroxyethyl starch has a molar substitution of 0.7.

3. The method according to claim 1, wherein said hydroxyethyl starch has a molar substitution of 0.45.

4. The method according to claim 1, wherein said organic acid salt is a salt of an organic acid ion that may be metabolized.

5. The method according to claim 4, wherein said organic acid ion is selected from the group consisting lactate, acetate, pyruvate, gluconate and succinate.

6. The method according to claim 1, wherein said solution does not comprise a biological buffer.

7. The method according to claim 1, wherein said solution is a terminally heat sterilized solution.

8. The method according to claim 1, wherein said solution has a pH between 4 and 6.5.

9. The method according to claim 1, wherein said solution further comprises sodium chloride.

10. A method for increasing the circulating volume of a hypovolemic subject comprising administering to said subject a plasma-like substance comprising an aqueous solution of at least one water soluble hydroxyethyl starch selected from the group consisting of a hydroxyethyl starch having an average molecular weight of 400,000 to 550,000 and a hydroxyethyl starch having an average molecular weight of 150,000 to 350,000 daltons and an organic acid salt of an ion selected from the group consisting of lactate, acetate, pyruvate, gluconate and succinate, wherein said solution has a pH between 4 and 6.5.

11. The method according to claim 10, wherein said hydroxyethyl starch has a molar substitution of 0.7.

12. The method according to claim 11, wherein said hydroxyethyl starch is hetastarch.

13. The method according to claim 10, wherein said hydroxyethyl starch has a molar substitution of 0.45.

14. The method according to claim 13, wherein said hydroxyethyl starch is pentastarch.

15. The method according to claim 10, wherein said solution does not comprise a biological buffer.

16. The method according to claim 10, wherein said solution is a terminally heat sterilized solution.

17. The method according to claim 10, wherein said solution further comprises sodium chloride.

18. A plasma-like substance comprising an aqueous solution of at least one water soluble hydroxyethyl starch selected from the group consisting of a hydroxyethyl starch having an average molecular weight of 400,000 to 550,000 daltons and a hydroxyethyl starch having an average molecular weight of 150,000 to 350,000 daltons and an organic acid salt; wherein
   said solution has at least one of the following characteristics:
   is terminally heat sterilized; and
   has a pH between 4 and 6.5.

19. The plasma-like substance according to claim 18, wherein said hydroxyethyl starch has a molar substitution of 0.7.

20. The plasma-like substance according to claim 18, wherein said hydroxyethyl starch has a molar substitution of 0.45.

21. The plasma-like substance according to claim 18, wherein said organic acid salt is a salt of an organic acid ion that may be metabolized.

22. The plasma-like substance according to claim 21, wherein said organic acid ion is selected from the group consisting lactate, acetate, pyruvate, gluconate and succinate.

23. The plasma-like substance according to claim 18, wherein said solution does not comprise a biological buffer.

24. The plasma-like substance according to claim 18, wherein said solution is a terminally heat sterilized solution.

25. The plasma-like substance according to claim 18, wherein said solution has a pH between 4 and 6.5.

26. The plasma like solution according to claim 18, wherein said solution further comprises sodium chloride.

27. A plasma-like substance comprising an aqueous solution of at least one water soluble hydroxyethyl starch selected from the group consisting of a hydroxyethyl starch having an average molecular weight of about 400,000 to 550,000 daltons and a hydroxyethyl starch having an average molecular weight of 150,000 to 350,000 daltons and an organic acid salt of an ion selected from the group consisting of lactate, acetate, pyruvate, gluconate and succinate, wherein said solution has a pH between 4 and 6.5.

28. The plasma-like substance according to claim 27, wherein said hydroxyethyl starch has a molar substitution of 0.7.

29. The plasma-like substance according to claim 28, wherein said hydroxyethyl starch is hetastarch.

30. The plasma-like according to claim 27, wherein said hydroxyethyl starch has a molar substitution of 0.45.

31. The plasma-like according to claim 30, wherein said hydroxyethyl starch is pentastarch.

32. The plasma-like according to claim 27, wherein said solution does not comprise a biological buffer.

33. The plasma-like according to claim 27, wherein said solution is a terminally heat sterilized solution.

34. The plasma like solution according to claim 27, wherein said solution further comprises sodium chloride.

* * * * *